(12) United States Patent
Rees et al.

(10) Patent No.: US 10,051,868 B2
(45) Date of Patent: Aug. 21, 2018

(54) METHODS AND COMPOSITIONS FOR REDUCING FUNGAL INFESTATION AND IMPROVING GRASS QUALITY

(71) Applicant: BAYER CROPSCIENCE LP, Research Triangle Park, NC (US)

(72) Inventors: Richard T. Rees, Chapel Hill, NC (US); James M. Rutledge, Durham, NC (US)

(73) Assignee: BAYER CROPSCIENCE LP, Research Triangle, NC (US)

( * ) Notice: Subject to any disclaimer, the term of this patent is extended or adjusted under 35 U.S.C. 154(b) by 53 days.

(21) Appl. No.: 15/075,903

(22) Filed: Mar. 21, 2016

(65) Prior Publication Data

US 2016/0278385 A1    Sep. 29, 2016

Related U.S. Application Data

(60) Provisional application No. 62/139,147, filed on Mar. 27, 2015.

(51) Int. Cl.
*A01N 63/00* (2006.01)
*A01N 47/12* (2006.01)

(52) U.S. Cl.
CPC .............. *A01N 63/00* (2013.01); *A01N 47/12* (2013.01)

(58) Field of Classification Search
None
See application file for complete search history.

(56) References Cited

U.S. PATENT DOCUMENTS

| | | | |
|---|---|---|---|
| 3,513,241 | A | 5/1970 | Hoyer et al. |
| 5,912,208 | A | 6/1999 | Hioki et al. |
| 6,358,938 | B1 | 3/2002 | Donnadieu et al. |
| 6,406,690 | B1 | 6/2002 | Peleg et al. |
| 8,632,767 | B2 | 1/2014 | Alig et al. |
| 8,722,717 | B2 | 5/2014 | Alig et al. |
| 8,916,595 | B2 | 12/2014 | Kiguchi et al. |
| 9,560,852 | B2 | 2/2017 | Wolfram et al. |
| 9,596,862 | B2 | 3/2017 | Andersch et al. |
| 2011/0033436 | A1* | 2/2011 | Chen ............. A01N 63/00 424/93.461 |
| 2012/0083463 | A1 | 4/2012 | Maue et al. |
| 2012/0270913 | A1 | 10/2012 | Kurahashi |
| 2015/0011389 | A1 | 1/2015 | Hellwege |

FOREIGN PATENT DOCUMENTS

| | | | |
|---|---|---|---|
| EP | 2460406 A1 | 6/2012 | |
| EP | 2259685 A2 | 12/2012 | |
| JP | 11000163 A | 1/1999 | |
| WO | WO-2014079814 A1 * | 5/2014 | ............. A01N 63/00 |

OTHER PUBLICATIONS

Agropedia ("Yellow leaf spot disease in sugarcane"; http://agropedia.iitk.ac.in/content/yellow-leaf-spot-disease-sugarcane; Internet Archive Wayback Machine, accessed on Dec. 10, 2017). (Year: 2012).*
International Search Report dated Jun. 10, 2016, issued in counterpart application No. PCT/US2016/023371.
"Environmental Information Sheet for Infinito" The Voluntary Initiative. EIS Version 7, (Feb. 2017) p. 1-2.
"Propamocarb HCl" British Columbia Ministry of Agriculture, Food and Fisheries (Updated Nov. 2004) p. 1-2.
Environmental Information Sheet for Flocter the Voluntary Initiative. EIS Version 1, (Apr. 2014) p. 1-2.
Soper et al. "Ability of Fungicides to Promote Turfgrass Health" University of Wisconsin-Madison. (2014) p. 1-2.
"Yellow Spot" Umass Amherst Turf Program. (Jul. 21, 2008) p. 1-2.

* cited by examiner

*Primary Examiner* — Michelle F Paguio Frising
(74) *Attorney, Agent, or Firm* — McBee Moore Woodward & Vanik IP, LLC; Susan McBee

(57) ABSTRACT

The disclosure provides methods for reducing fungal infestation to a crop or plant by applying a composition including propamocarb and *Bacillus firmus* to a crop or plant. Methods of reducing yellow spot infestation to a plant or crop are also described herein. The disclosure also provides for compositions and methods of improving turfgrass and/or ornamental grass quality.

16 Claims, 3 Drawing Sheets

FIG. 1

| Treatment and rate per 1000 ft² | 23 May Quality[z] | 23 May Color[z] | 20 June Quality | 20 June Color | 18 July Quality | 18 July Color | 12 August Quality | 12 August Color |
|---|---|---|---|---|---|---|---|---|
| 1. Control | 7.7 | 6.3 | 7.3 | 6.7 | 6.3 | 7.0 | 6.7 | 6.7 |
| 2. Propamocarb-HCl–2.0 fl oz | 7.7 | 6.3 | 7.0 | 7.3 | 6.7 | 7.0 | 7.0 | 6.3 |
| 3. Propamocarb-HCl–2.0 fl oz + Bacillus firmus–12.9 oz. | 7.3 | 6.0 | 7.7 | 7.7 | 7.3 | 7.0 | 7.3 | 7.0 |
| 4. Bacillus firmus–12.9 oz. | 7.3 | 6.0 | 6.7 | 7.3 | 7.0 | 7.0 | 7.0 | 7.0 |

[z] Both turf quality and color were rated on a scale of 0-9, with 9 being the highest possible quality and color and 0 being dead, brown turf.

FIG. 2

| Treatment formulation, rate 1000 ft$^{-2}$ | Application code$^x$ | Turf quality$^y$ | | | |
|---|---|---|---|---|---|
| | | 18 Jun | 16 Jul | 13 Aug | 2 Sep |
| 1. Propamocarb-HCl-2.0 fl oz | AEIMQ | 5.0 | 4.6 | 5.9 | 5.3 a |
| 2. Propamocarb-HCl-2.0 fl oz + Bacillus firmus-12.9 oz. | AEIMQ | 6.1 | 5.0 | 5.4 | 5.7 a |
| 3. Bacillus firmus-12.9 oz. | AEIMQ | 5.3 | 4.4 | 5.1 | 5.5 a |
| 4. Untreated control | AEIMQ | 4.8 | 4.5 | 5.7 | 5.0 a |

$^x$ Application code indicates date of each treatment: A = 24 April, E = 22 May, I = 18 June, M = 17 July, Q = 14 August.

$^y$ Turfgrass quality is on a 1-9 scale (9 = best, 6 = acceptable) based on color, density, and uniformity.

FIG. 3

| Treatment formulation, rate 1000 ft$^{-2}$ | Application code[x] | Yellow spot incidence (%) | |
|---|---|---|---|
| | | 16 Jul | 2 Sep |
| 1. Propamocarb-HCl-2.0 fl oz | AEIMQ | 22.1 | 13.9 |
| 2. Propamocarb-HCl-2.0 fl oz + *Bacillus firmus*-12.9 oz. | AEIMQ | 14.2 | 0.5 |
| 3. *Bacillus firmus*-12.9 oz. | AEIMQ | 18.8 | 1.3 |
| 4. Untreated control | AEIMQ | 20.9 | 17.7 |

[x] Application code indicates date of each treatment: A = 24 April, E = 22 May, I = 18 June, M = 17 July, Q = 14 August.

METHODS AND COMPOSITIONS FOR REDUCING FUNGAL INFESTATION AND IMPROVING GRASS QUALITY

CROSS REFERENCE TO RELATED APPLICATIONS

This application claims priority to 62/139,147 filed Mar. 27, 2015, the content of which is incorporated herein by reference in its entirety.

FIELD

The disclosure provides for compositions and methods comprising propamocarb and *Bacillus firmus*. The disclosure further provides for compositions and methods of reducing yellow spot infestation to a plant or crop. The disclosure also provides for compositions and methods of improving turfgrass and/or ornamental grass quality.

BACKGROUND

There is a need to develop compositions and/or methods that are capable of reducing yellow spot infestation to a plant or crop, and for improving turfgrass and/or ornamental grass quality. To this end, the disclosure provides for formulations comprising a combination of propamocarb and *Bacillus firmus* capable of reducing yellow spot infestation to a plant or crop and for improving turfgrass and/or ornamental grass quality. The issue of yellow spot is becoming more prevalent, particularly in the northern United States, due to the effects of climate change. In particular, the issue of yellow spot is becoming more prevalent due to hotter summers and large swings in excessive rainfall, along with restrictions on chemistries that in the past have adequately dealt with some bacterial diseases such as yellow spot.

SUMMARY

In an aspect, the disclosure provides for a method of reducing or controlling damage from yellow spot in a plant or crop, for example yellow spot disease in turfgrass, by treating soil, a seed, a plant, and/or a plant part with a composition including
   a) propamocarb; and
   b) *Bacillus firmus*.

In another aspect, the disclosure provides for a method of improving plant color and quality by treating soil, a seed, a plant, a leaf, and/or a plant part with a composition including
   a) propamocarb; and
   b) *Bacillus firmus*.

The disclosure further provides for a composition comprising a synergistic combination of
   a) propamocarb; and
   b) *Bacillus firmus*.

In an aspect, the disclosure provides for a method described herein, for example, a method of reducing or controlling yellow spot disease, and/or a method of improving plant quality and color, wherein soil, a seed, a plant, and/or a plant part is treated with a synergistic composition including
   a) propamocarb; and
   b) *Bacillus firmus*.

In another aspect, the disclosure provides for a method described herein, wherein a composition combination including a) and b) is applied to a plant part:
   a) propamocarb-HCl in an application amount from about 2 to 4.5 fl. oz/1000 ft$^2$; and
   b) 5% *Bacillus firmus* in an application amount from about 6 to 24 oz/1000 ft$^2$.

In another aspect, the disclosure provides for methods of treating yellow spot with a composition or method described herein.

Seeds, plants, and/or plant parts treated with compositions described herein are also envisioned.

Turf health was better improved in the absence of disease by the combination of components propamocarb and *Bacillus firmus* compared to the components alone.

BRIEF DESCRIPTION OF THE FIGURES

FIG. 1 depicts turfgrass (*Agrostic palustris* "Penncross" and "Penneagle") quality and color at various intervals on a scale of 0 (lowest possible quality) to 9 (highest possible quality) for treatments 1-4 at defined application amounts.

FIG. 2 depicts turfgrass (*Agrostic palustris* "Al") quality and color at various intervals on a scale of 0 (lowest possible quality) to 9 (highest possible quality) for treatments 1-4 at defined application amounts.

FIG. 3 depicts yellow spot incidence (%) in turfgrass (*Agrostic palustris* "Al") for treatments 1-4 at defined application amounts.

DETAILED DESCRIPTION

Propamocarb is a known fungicidal active compound which is represented by the following formula (I):

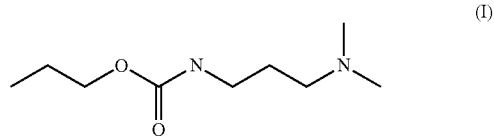

(I)

Propamocarb is described in British patent GB-1212708, which is hereby incorporated by reference in its entirety. Derivatives of propamocarb are exemplified by the following compounds:

(a) Propamocarb-hydrochloride, or propamocarb-HCl, is a known compound having the chemical name propyl [3-(dimethylamino)propyl]carbamate hydrochloride, and is represented by the following formula (Ia):

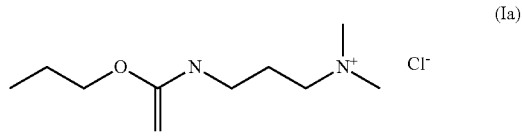

(Ia)

(b) Propamocarb-fosetylate, or dimethyl-(propoxycarbonylamino)propyl]ammonium O-ethylphosphonate, is represented by the following formula (Ib):

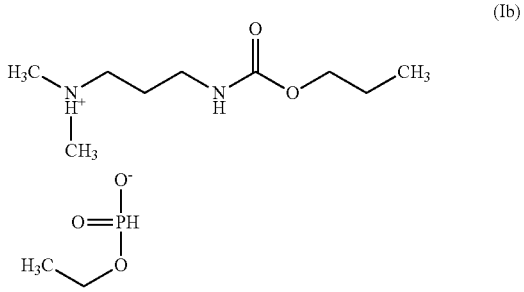

(Ib)

(c) Phosphoric acid derivatives of propamocarb, such as dimethyl-[3-(propoxy-carbonylamino)propyl]-ammonium phosphate and dimethyl-[3-(propoxycarbonyl-amino)propyl]ammonium phosphate;

(d) All fungicially active organic or inorganic salts of propamocarb.

*Bacillus firmus*, a spore-forming bacterium of the genera *Bacillus*, is a known nematicidal agent. A description of nematicidal activity of *Bacillus firmus* is found in WO-A 1996/32840, which is hereby incorporated in its entirety.

*Bacillus firmus* is currently being used as a nematicide. However, by way of the current disclosure, it is observed that compositions comprising the combination of propamocarb and *Bacillus firmus* demonstrate unexpected properties on reducing yellow spot infestation to a plant or crop and on improving turfgrass and/or ornamental grass quality.

*Bacillus firmus* has plant health properties but these properties are attributed to the soil. Propamocarb is a fungicide for a fungal pathogen, Pythium blight or root rot of turf.

Yellow spot is a bacterial pathogen and is not controlled by *Bacillus firmus* (a nematicide) or propamocarb (a fungicide) alone. Compositions comprising *Bacillus firmus* and propamocarb controlled the yellow spot disease.

Turfgrasses include all grasses such as St. Augustine grass, bermudagrass, bahiagrass, buffalograss, centipedegrass, Kentucky bluegrass, fine fescue, tall fescue, perennial ryegrass, creeping bentgrass, zoysiagrass, crabgrass, guineagrass, pangolagrass, torpedograss, and tropical carpetgrass. Species of turfgrass include creeping bentgrass, which includes “Penncross”, “Penneagle”, and “Al”.

Seeds, plants, and plant parts treated with compositions described herein are also provided for by the disclosure.

Propamocarb HCl is a protectant fungicide with systemic activity and is absorbed by roots and leaves and then transported upwards in the plant. Propamocarb has activity against several oomycete (water mold) fungi which cause seed, seedling, root and stem rots and foliar diseases.

The disclosure provides for a method of reducing plant, root, or plant part damage by treating soil, a seed, plant, root, and/or plant part with one of more active agents described herein. The disclosure provides for a method of reducing plant, root, or plant part damage by treating soil, a seed, plant, root, and/or plant part with a composition comprising *Bacillus firmus* and propamocarb.

In an aspect, the disclosure provides for a composition comprising, consisting of, or consisting essentially of one or more repelling, controlling, or directing compositions disclosed herein.

The method comprises the step of applying a foliar treatment composition at least once to established plants, wherein the treatment composition comprises propamocarb and *Bacillus firmus*. The foliar treatment composition may be applied additional times at appropriate intervals as necessary. The foliar treatment composition may or may not be watered in to the thatch layer.

In an aspect, the disclosure provides for a method of reducing plant, root, or plant part damage by treating a soil, a seed, plant, root, or plant part with a composition comprising propamocarb and *Bacillus firmus*.

In another aspect, the disclosure provides for a method of reducing plant, root, or plant part damage by treating soil, a seed, plant, root, or plant part with propamocarb and *Bacillus firmus*. In yet another aspect, the disclosure provides for a method of reducing plant, root, or plant part damage by treating a seed, plant, root, or plant part with a synergistic combination of propamocarb and *Bacillus firmus*.

In an aspect, the disclosure provides for a method of reducing plant, root, or plant part damage by treating soil, a seed, plant, root, or plant part with propamocarb and *Bacillus firmus*. The disclosure also provides for synergistic composition and/or methods comprising, consisting essentially of, or consisting of propamocarb and *Bacillus firmus*. In an aspect, synergistic composition and/or methods comprising, consisting essentially of, or consisting of propamocarb and *Bacillus firmus*.

In a further aspect, the disclosure provides for a method of controlling damage, reducing damage, and/or increasing plant yield comprising a plant drench application of a composition comprising, consisting essentially of, or consisting of propamocarb and *Bacillus firmus* as a plant drench application.

In another aspect, the disclosure provides for a method of controlling damage, reducing damage, and/or increasing plant yield comprising an in-furrow application of a composition comprising, consisting essentially of, or consisting of propamocarb and *Bacillus firmus* as a plant drench application.

In a further aspect, the disclosure provides for use of a composition comprising, consisting essentially of, or consisting of propamocarb and *Bacillus firmus* in a method of treating yellow spot disease. In another aspect, the disclosure provides for use of a composition comprising, consisting essentially of, or consisting of propamocarb and *Bacillus firmus* in a method of treating yellow spot disease.

In conjunction with the present invention, “controlling” denotes a preventive, treatment, or curative reduction of the damage in comparison to the untreated plant or crop, more preferably the infestation is essentially repelled, most preferably the infestation is totally suppressed.

In an aspect, the amount of a controlling, damage reducing, or yield increasing composition described herein can be an amount that is effective (“effective amount”) to protect seeds, plant parts, or plants against damage or pest infestation and/or increase plant yield.

In an aspect, a composition described herein is applied to a seed, soil, plant, or plant part from about 6 to about 24 oz/1000 $ft^2$ of *Bacillus firmus* and from about 2 to about 4.5 fl. oz/1000 $ft^2$ of propamocarb. In a further aspect, a composition described herein is applied to a seed, soil, plant, or plant part at about 12.9 oz/1000 $ft^2$ *Bacillus firmus* and about 2 fl. oz/1000 $ft^2$ of propamocarb.

In an aspect, a composition described herein is applied to a leaf from about 6 to about 24 oz/1000 $ft^2$ of *Bacillus firmus* and from about 2 to about 4.5 fl. oz/1000 $ft^2$ of propamocarb. In a further aspect, a composition described herein is applied to a leaf at about 12.9 oz/1000 $ft^2$ *Bacillus firmus* and about 2 fl. oz/1000 $ft^2$ of propamocarb.

In an aspect, a composition described herein is applied to turfgrass from about 6 to about 24 oz/1000 $ft^2$ of *Bacillus*

*firmus* and from about 2 to about 4.5 fl. oz/1000 ft$^2$ of propamocarb. In a further aspect, a composition described herein is applied to turfgrass at about 12.9 oz/1000 ft$^2$ *Bacillus firmus* and about 2 fl. oz/1000 ft$^2$ of propamocarb.

In an aspect, a composition described herein is applied to creeping bentgrass from about 6 to about 24 oz/1000 ft$^2$ of *Bacillus firmus* and from about 2 to about 4.5 fl. oz/1000 ft$^2$ of propamocarb. In a further aspect, a composition described herein is applied to creeping bentgrass at about 12.9 oz/1000 ft$^2$ *Bacillus firmus* and about 2 fl. oz/1000 ft$^2$ of propamocarb.

In yet another aspect, a composition described herein is applied to a leaf in a manner sufficient to convey the desired property, for example, improved color or quality or reduction in yellow spot.

In an aspect, a composition disclosed herein is formulated as a foliar composition, a foliar spray, solutions, emulsions, suspension, coating formulation, non-pesticidal or pesticidal coating formulation, encapsulated formulation, solid, liquid, fertilizer, paste, granule, powder, suspension, or suspension concentrate. In another aspect, a composition described herein may be employed alone or in solid, dispersant, or liquid formulation. In yet another aspect, a composition described herein is formulated as a tank-mix product.

These formulations are produced in a known manner, for example by mixing the active compounds with extenders, that is liquid solvents, pressurized liquefied gases and/or solid carriers, optionally with the use of surface-active agents, that is emulsifiers and/or dispersants and/or foam formers. If the extender used is water, it is also useful to employ for example organic solvents as cosolvents. Suitable liquid solvents are essentially: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, and also water. Liquefied gaseous extenders or carriers are those liquids which are gaseous at ambient temperature and at atmospheric pressure, for example aerosol propellants such as halogenated hydrocarbons and also butane, propane, nitrogen and carbon dioxide. As solid carriers there are suitable: for example ground natural minerals, such as kaolins, clays, talc, chalk, quartz, attapulgite, montmorillonite or diatomaceous earth, and ground synthetic minerals, such as finely divided silica, alumina and silicates. As solid carriers for granules there are suitable: for example crushed and fractionated natural rocks such as calcite, pumice, marble, sepiolite and dolomite, and also synthetic granules of inorganic and organic meals, and granules of organic material such as sawdust, coconut shells, maize cobs and tobacco stalks. As emulsifiers and/or foam formers there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and protein hydrolysates. As dispersants, for example, lignosulphite waste liquors and methylcellulose are suitable.

Tackifiers such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other possible additives are mineral and vegetable oils.

Colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc, can also be used.

Plants are understood as meaning, in the present context, all plants and plant populations, such as desired and undesired wild plants or crop plants (including naturally occurring crop plants). Crop plants or crops may be plants which can be obtained by conventional breeding and optimization methods or else by biotechnological and genetic engineering methods or by combinations of these methods, including the transgenic plants and including the plant varieties capable or not capable of being protected by plant breeders' rights.

In an aspect, a composition described herein is applied to a soil, plant, crop, seed, leaf, or plant part thereof in a single application step. In another aspect, a composition described herein is applied to a plant, crop, seed, leaf, or plant part thereof in multiple application steps, for example, two, three, four, five or more application steps. In another aspect, the second, third, fourth, or fifth or more application steps may be with the same or different compositions. The methods described herein also provide for an aspect where multiple application steps are excluded.

In an aspect, a composition described herein is applied to a plant, crop, seed, or plant part thereof one or more times during a growing, planting, or harvesting season. In another aspect, a compound or composition described herein is applied to a plant, crop, seed, or plant part thereof in one, two, three, four, or five or more times during a growing, planting, or harvesting season. In another aspect, a compound or composition described herein is applied to a plant, crop, seed, or plant part thereof only one time, no more than two times, or no more than three times during a growing, planting, or harvesting season. In yet another aspect, a compound or composition is applied in a single step to a seed. In yet another aspect, a seed described herein is planted in a one-pass application step.

In another aspect, the disclosure provides for pre-plant, pre-emergent, post-emergent, application steps or combinations thereof. In another aspect, a compound or composition described herein is first applied in a pre-plant step and followed by one or more pre-emergent or post-emergent steps. In yet another aspect, the disclosure provides for only a pre-plant step.

Methods described herein can be used in the treatment of genetically modified organisms (GMOs), e.g., plants or seeds. Genetically modified plants (or transgenic plants) are plants of which a heterologous gene has been stably integrated into genome. The expression "heterologous gene" essentially means a gene which is provided or assembled outside the plant and when introduced in the nuclear, chloroplastic or mitochondrial genome gives the transformed plant new or improved agronomic or other properties by expressing a protein or polypeptide of interest or by down-regulating or silencing other gene(s) which are present in the plant (using for example, antisense technology, cosuppression technology or RNA interference—RNAi-technology). A heterologous gene that is located in the genome is also called a transgene. A transgene that is defined by its particular location in the plant genome is called a transformation or transgenic event.

In an aspect, plants can be obtained by traditional breeding and optimization methods or by biotechnological and recombinant methods, or combinations of these methods, including the transgenic plants and including the plant varieties which are capable or not capable of being protected by Plant Breeders' Rights.

In another aspect, plant species and plant varieties which are found in the wild or which are obtained by traditional biological breeding methods, such as hybridization or protoplast fusion, and parts of these species and varieties are treated. In a further preferred embodiment, transgenic plants and plant varieties which were obtained by recombinant methods, if appropriate in combination with traditional methods (genetically modified organisms) and their parts are treated.

Plant parts should be understood as meaning all above ground and subsoil parts and organs of plants, such as shoot, leaf, flower, root, leaves, needles, stalks, stems, fruiting bodies, fruits and seeds, tubers and rhizomes. Plant parts also include harvested crops, and also vegetative and generative propagation material, for example cuttings, tubers, rhizomes, slips and seeds.

Seeds, plant parts, leaves, and plants may be treated with the described compositions by applying the compounds or compositions directly to the seed, plant part, leaf, or plant. In another aspect, the seed, plant part, leaf, or plant may be treated indirectly, for example by treating the environment or habitat in which the seed, plant part, leaf, or plant is exposed to. Conventional treatment methods may be used to treat the environment or habitat including dipping, spraying, fumigating, chemigating, fogging, scattering, brushing on, shanking or injecting.

According to the invention the treatment of the plants and seeds with a composition described herein, can be carried out directly by the customary treatment methods, for example by immersion, spraying, vaporizing, fogging, injecting, dripping, drenching, broadcasting or painting, and seed treatment.

In another aspect, a composition herein treats or reduces yellow spot disease. Yellow spot appears in the form of yellow, chlorotic, circular discrete patches ranging from dime/quarter size up to 2-3 inches diameter on bentgrass putting greens, tees, and approaches. The primary causal agent of the disease is not fully understood but has been suggested to be cyanobacteria causing blue-green algae.

In an aspect, a compound or composition described herein is formulated as a foliar composition, a foliar spray, solution, emulsion, coating formulation, non-pesticidal or pesticidal coating formulation, encapsulated formulation, solid, liquid, fertilizer, paste, granule, powder, suspension, or suspension concentrate. In another aspect, a compound or composition described herein may be employed alone or in solid, dispersant, or liquid formulation. In yet another aspect, a compound or composition described herein is formulated as a tank-mix product.

In another aspect, a compound or composition described herein can take any of a variety of dosage forms including, without limitation, suspension concentrates, aerosols, capsule suspensions, cold-fogging concentrates, warm-fogging concentrates, encapsulated granules, fine granules, flowable concentrates for the treatment of seed, ready-to-use solutions, dustable powders, emulsifiable concentrates, oil-in-water emulsions, water-in-oil emulsions, macrogranules, microgranules, oil-dispersible powders, oil-miscible flowable concentrates, oil-miscible liquids, foams, pastes, pesticide-coated seed, suspoemulsion concentrates, soluble concentrates, wettable powders, soluble powders, dusts and granules, water-soluble granules or tablets, water-soluble powders for the treatment of seed, wettable powders, natural products and synthetic substances impregnated with a compound or composition described herein, a net impregnated with a compound or composition described herein, and also microencapsulations in polymeric substances and in coating materials for seed, and also ULV cold-fogging and warm-fogging formulations.

In another aspect, a composition disclosed herein may optionally include one or more additional compounds providing an additional beneficial or otherwise useful effect. Such compounds include, without limitation, an adhesive, a surfactant, a solvent, a wetting agent, an emulsifying agent, a carrier, an adjuvant, a diluent, a dispersing agent an insecticide, a pesticide, a fungicide, a fertilizer of a micronutrient or macronutrient nature, a herbicide, a feeding inhibitor, an insect molting inhibitor, an insect mating inhibitor, an insect maturation inhibitor, a nematocide, a nutritional or horticultural supplement, or any combination thereof. In an aspect, a composition described herein is odor free.

In another aspect, a compositions described herein can be combined with a fertilizer. Examples of fertilizers capable of being used with the compositions and methods described herein include, for example, urea, ammonium nitrate, ammonium sulfate, calcium nitrate, diammonium phosphate, monoammonium phosphate, triple super phosphate, potassium nitrate, potassium nitrate, nitrate of potash, potassium chloride, muriate of potash, di- and mono-potassium salts of phosphite/phosphonate.

As previously mentioned, yellow spot is a bacterial pathogen and is not controlled by either propamocarb (a fungicide) or *Bacillus firmus* (a nematicide) alone. Therefore, it s unexpected that the combination of propamocarb and *Bacillus firmus* has the synergistic effects disclosed herein.

Kit

In another aspect, the disclosure provides for a kit comprising, consisting essentially of, or consisting of any of the compounds or compositions disclosed herein. In an aspect, the kit includes any of the combination of compounds or compositions described in Examples 1-2 or FIGS. 1-3. In another aspect, the kit provides for the compositions described in Examples 1-2 or FIGS. 1-3, applied in a manner that is consistent with the methodology of these examples and figures. In another aspect, the kit provides instructions or guidance regarding the use of the compositions or methods described herein.

In an aspect, the kit includes instructions describing the methodology described herein. In another aspect, the kit includes instructions describing the methodology set forth in any of Examples 1-2 or FIGS. 1-3. In an aspect, the instructions are included with the kit, separate from the kit, in the kit, or are included on the kit packaging.

The following examples serve to illustrate certain aspects of the disclosure and are not intended to limit the disclosure.

EXAMPLES

Example 1

Example 1 discloses the effect of *Bacillus firmus* and propamocarb-HCl on quality improvement of greens height turf, creeping bentgrass (*Agrostis palustris* "Penncross" and "Penneagle").

Tests were conducted on a Bridgehampton silt loam. The turf was maintained at a 0.125-inch mowing height, irrigated as needed, and a total of 4 lb N was applied in four separate applications throughout the course of the season as a slow release formulation. Plots were measured 5 ft×5 ft with no borders, and were arranged in a randomized complete block design with three replicates on an original mixture of 83% "Penncross" and 17% "Penneage" creeping bentgrass with approximately 5% *Poa annua* invasion. Fungicides were applied using a $CO_2$-pressurized hand-held sprayer fitted with TeeJet 8004VS Visiflow flat fan nozzles delivering 3.2 gal/1000 ft² at 40 psi. Applications were made on a 28-day schedule beginning on 23 May and continuing on 20 June, 16 July, and 12 August. Materials were watered into turf with approximately 0.5" of irrigation, measured by tin can. Ratings were taken just prior to each application. Chlorothanonil was applied on a 10-14 day schedule as needed, to manage dollar spot, which had just begun to appear by the second rating date.

During the length of the trial, no observable differences were noticed in turfgrass quality or turfgrass coverage. Consequently, only turfgrass quality and turfgrass color data are reported. During the test period, *Bacillus firmus* and *Bacillus firmus*+propamocarb-HCl treatments resulted in slightly darker turf than the propamocarb-HCl or control treatments. The *Bacillus firmus*+propamocarb-HCl treatment provided the best quality, often the best color following the first rating. However, all of the treatments performed well and the data reported below in Table 1 (and as shown in FIG. 1) should not be used to make inferences about improved quality and color due to the lack of statistical significance.

TABLE 1

| Treatment and rate per 1000 ft² | 23 May Quality$^z$ | 23 May Color$^z$ | 20 June Quality | 20 June Color | 18 July Quality | 18 July Color | 12 August Quality | 12 August Color |
|---|---|---|---|---|---|---|---|---|
| 1. Control | 7.7 | 6.3 | 7.3 | 6.7 | 6.3 | 7.0 | 6.7 | 6.7 |
| 2. Propamocarb-HCl-2.0 fl oz | 7.7 | 6.3 | 7.0 | 7.3 | 6.7 | 7.0 | 7.0 | 6.3 |
| 3. Propamocarb-HCl-2.0 fl oz + *Bacillus firmus*-12.9 oz. | 7.3 | 6.0 | 7.7 | 7.7 | 7.3 | 7.0 | 7.3 | 7.0 |
| 4. *Bacillus firmus*-12.9 oz. | 7.3 | 6.0 | 6.7 | 7.3 | 7.0 | 7.0 | 7.0 | 7.0 |

$^z$Both turf quality and color were rated on a scale of 0-9, with 9 being the highest possible quality and color and 0 being dead, brown turf.

Example 2

Example 2 discloses the effect of *Bacillus firmus* and propamocarb-HCl on quality improvement of greens height turf, creeping bentgrass (*Agrostis palustris* A1).

The study was conducted on "A-1" creeping bentgrass maintained as a golf course putting green. Plots were mowed 6 times per week with clippings collected. The study was irrigated to prevent drought stress. Individual plots were 3 ft×6 ft and arranged in a randomized complete block design with 4 replications. Chipco 26GT (4 fl oz/1000 ft²) was applied to the study for suppression of dollar spot and brown patch on 2 May, 9 June, 29 July, and 20 August. Treatments were applied in water equivalent to 2 gal 1000 ft-2 with a $CO_2$-powered sprayer equipped with a TeeJet AI9508E nozzle at 50 psi. Treatments were initiated on 24 April and applied on 28-day intervals. The study was irrigated with 0.1-0.2 inches of water after all treatments were applied. Percent turf area exhibiting yellow spot symptoms was assessed on 24 June, 16 July, and 2 September. Turfgrass quality was assessed on 24 April, 21 May, 18 June, 16 July, 13 August, and 2 September. NDVI was assessed on 21 May, 18 June, 17 July, 13 August, and 2 September. Root length (3 subsamples per plot) was assessed on 18 September.

Results:

Turf quality is depicted below in Table 2 (and shown in FIG. 2). An epidemic of yellow spot occurred in late June and persisted into September. The highest severity within the controls was observed on 16 July with 20.9%. On 2 September, the propamocarb-HCl+*Bacillus firmus* treatment and *Bacillus firmus* (alone) exhibited significantly less yellow spot compared to the control, as shown in Table 3 (and FIG. 3). Propamocarb-HCl+*Bacillus firmus* improved turf quality on 18 June.

TABLE 2

| Treatment formulation, rate 1000 ft⁻² | Application code$^x$ | Turf quality$^y$ 18 Jun | 16 Jul | 13 Aug | 2 Sep |
|---|---|---|---|---|---|
| 1. Propamocarb-HCl-2.0 fl oz | AEIMQ | 5.0 | 4.6 | 5.9 | 5.3 a |
| 2. Propamocarb-HCl-2.0 fl oz + *Bacillus firmus*-12.9 oz. | AEIMQ | 6.1 | 5.0 | 5.4 | 5.7 a |
| 3. *Bacillus firmus*-12.9 oz. | AEIMQ | 5.3 | 4.4 | 5.1 | 5.5 a |
| 4. Untreated control | AEIMQ | 4.8 | 4.5 | 5.7 | 5.0 a |

$^x$Application code indicates date of each treatment: A = 24 April, E = 22 May, I = 18 June, M = 17 July, Q = 14 August.
$^y$Turfgrass quality is on a 1-9 scale (9 = best, 6 = acceptable) based on color, density, and uniformity.

TABLE 3

| Treatment formulation, rate 1000 ft⁻² | Application code$^x$ | Yellow spot incidence (%) 16 Jul | 2 Sep |
|---|---|---|---|
| 1. Propamocarb-HCl-2.0 fl oz | AEIMQ | 22.1 | 13.9 |
| 2. Propamocarb-HCl-2.0 fl oz + *Bacillus firmus*-12.9 oz. | AEIMQ | 14.2 | 0.5 |
| 3. *Bacillus firmus*-12.9 oz. | AEIMQ | 18.8 | 1.3 |
| 4. Untreated control | AEIMQ | 20.9 | 17.7 |

$^x$Application code indicates date of each treatment: A = 24 April, E = 22 May, I = 18 June, M = 17 July, Q = 14 August.

The invention claimed is:
1. A composition comprising
   a) propamocarb; and
   b) *Bacillus firmus*
   wherein said composition reduces or controls yellow spot in a plant when treating soil, a seed, a plant, and/or a plant part with a composition comprising a) and b), and wherein a) and b) are the sole active components in the composition.
2. The composition of claim 1, wherein component (a) is propamocarb-HCl.

3. The composition of claim 1, wherein the weight ratio of propamocarb to *Bacillus firmus* is 0.75:1-1:12.

4. A composition according to claim 1, comprising a synergistic combination of
   a) propamocarb; and
   b) *Bacillus firmus*,
   wherein said composition synergistically reduces yellow spot damage relative to the expected amount of the same separate application amount of a) propamocarb and b) *Bacillus firmus*.

5. A kit comprising a composition of claim 1.

6. A method of reducing or controlling yellow spot in a plant or crop comprising treating soil, a seed, a plant, and/or a plant part with a composition according to claim 1.

7. The method of claim 6, wherein component (a) is propamocarb-HCl.

8. The method of claim 6, comprising treating soil, a seed, a plant, and/or a plant part with a composition comprising:
   a) propamocarb-HCl in an application amount from about 2 to about 4.5 fl. oz/1000 ft$^2$; and
   b) 5% *Bacillus firmus* in an application amount from about 6 to about 24 oz/1000 ft$^2$.

9. The method of claim 6, comprising treating soil, a seed, a plant, and/or a plant part with a composition comprising:
   a) propamocarb-HCl in an application amount of about 2 fl. oz/1000 ft$^2$; and
   b) 5% *Bacillus firmus* in an application amount of about 12.9 oz/1000 ft$^2$.

10. The method according to claim 6, wherein said composition is applied as a foliar treatment.

11. The method according to claim 6, wherein said composition is applied as a treatment to one or more turfgrass leaves.

12. A method of reducing or controlling yellow spot in a plant or crop comprising treating soil, a seed, a plant, and/or a plant part with a composition of claim 1 that consists essentially of:
   a) propamocarb; and
   b) *Bacillus firmus*.

13. A method of improving turfgrass quality comprising treating soil, a seed, a plant, and/or a plant part with a composition according to claim 1.

14. The method of claim 13, comprising treating soil, a seed, a plant, and/or a plant part with a composition comprising:
   a) propamocarb-HCl in an application amount from about 2 to about 4.5 fl. oz/1000 ft$^2$; and
   b) 5% *Bacillus firmus* in an application amount from about 6 to about 24 oz/1000 ft$^2$.

15. The method of claim 13, comprising treating soil, a seed, a plant, and/or a plant part with a composition comprising:
   a) propamocarb-HCl in an application amount of about 2 fl. oz/1000 ft$^2$; and
   b) 5% *Bacillus firmus* in an application amount of about 12.9 oz/1000 ft$^2$.

16. The method according to claim 13, wherein said composition is applied as a foliar treatment.

* * * * *